(12) United States Patent
McGuckin, Jr.

(10) Patent No.: US 10,368,975 B2
(45) Date of Patent: Aug. 6, 2019

(54) ESOPHAGEAL SLEEVE

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

(21) Appl. No.: 15/893,545

(22) Filed: Feb. 9, 2018

(65) Prior Publication Data

US 2018/0161145 A1 Jun. 14, 2018

Related U.S. Application Data

(62) Division of application No. 14/859,283, filed on Sep. 19, 2015, now Pat. No. 9,901,436.

(60) Provisional application No. 62/062,344, filed on Oct. 10, 2014.

(51) Int. Cl.
| | |
|---|---|
| *A61F 2/04* | (2013.01) |
| *A61F 2/88* | (2006.01) |
| *A61F 5/00* | (2006.01) |
| *A61B 17/00* | (2006.01) |
| *A61F 2/24* | (2006.01) |
| *A61F 2/95* | (2013.01) |

(52) U.S. Cl.
CPC .............. *A61F 2/04* (2013.01); *A61F 2/88* (2013.01); *A61F 5/0079* (2013.01); *A61B 2017/00827* (2013.01); *A61F 2/2412* (2013.01); *A61F 2/95* (2013.01); *A61F 2002/044* (2013.01); *A61F 2002/9528* (2013.01); *A61F 2220/0016* (2013.01); *A61F 2230/0091* (2013.01); *A61F 2250/0059* (2013.01)

(58) Field of Classification Search
CPC ............. A61F 2002/044; A61F 5/0079; A61B 2017/00827
See application file for complete search history.

(56) References Cited

U.S. PATENT DOCUMENTS

| | | | |
|---|---|---|---|
| 6,264,700 | B1 | 7/2001 | Kilcoyne et al. |
| 2001/0020190 | A1 | 9/2001 | Taylor |
| 2003/0212450 | A1 | 11/2003 | Schlick |
| 2004/0102855 | A1 | 5/2004 | Shank |

(Continued)

FOREIGN PATENT DOCUMENTS

| | | | | |
|---|---|---|---|---|
| EP | 0808614 | | 11/1997 | |
| EP | 1360942 | | 11/2003 | |
| WO | WO 2015195266 | A1 * | 12/2015 | ............... A61F 2/04 |

OTHER PUBLICATIONS

The Extended European Search Report Application No. 15187986.3 dated Mar. 14, 2016.

*Primary Examiner* — Megan Y Wolf
(74) *Attorney, Agent, or Firm* — Neil D. Gershon

(57) ABSTRACT

A device for treating acid reflux comprising a sleeve configured and dimensioned for insertion into the esophagus of the patient, the sleeve having a proximal portion, a distal portion and an intermediate portion between the distal and proximal portions. The sleeve includes a an inner member applying a radial force on the sleeve for securement within the esophagus, and a skirt connected to the sleeve to block acid backup from the stomach while not inhibiting passage of food into the stomach.

13 Claims, 6 Drawing Sheets

(56) References Cited

U.S. PATENT DOCUMENTS

| | | | |
|---|---|---|---|
| 2004/0225353 A1* | 11/2004 | McGuckin, Jr. | A61F 2/2412 623/2.11 |
| 2010/0121461 A1 | 5/2010 | Sobrino-Serrano | |
| 2010/0256775 A1 | 10/2010 | Belhe et al. | |
| 2013/0345670 A1 | 12/2013 | Rajagopalan | |
| 2014/0156020 A1 | 6/2014 | Blackmon | |

* cited by examiner

ESOPHAGEAL SLEEVE

This application is a divisional of application Ser. No. 14/859,283, filed Sep. 19, 2015, now U.S. Pat. No. 9,901,436, which claims priority from provisional application Ser. No. 62/062,344, filed Oct. 10, 2014. The entire contents of each of these applications are incorporated herein by reference.

BACKGROUND OF THE INVENTION

1. Field of the Invention

This application relates to an esophageal sleeve, and, more particularly, to an esophageal sleeve to inhibit acid reflux while not inhibiting swallowing.

2. Background of the Related Art

Acid reflux disease is a condition in which the esophagus becomes irritated or inflamed because of acid backing off from the stomach. The esophagus stretches from the throat to be stomach, and when food is swallowed, it travels down the esophagus. Normally, the lower esophageal sphincter prevents the backing up of acid. During swallowing, the sphincter allows food to pass. It then tightens to prevent flow in the opposite direction. With acid reflux disease, the sphincter relaxes between swallows, allowing stomach contents and corrosive acid to well up and damage the lining of the esophagus.

The need exists for an easily implantable device for effectively treating acid reflux.

SUMMARY

The present invention advantageously provides a minimally invasive sleeve for treating acid reflux without inhibiting swallowing.

In one aspect, the present invention provides a device for treating acid reflux comprising a sleeve configured and dimensioned for insertion into the esophagus of the patient, the sleeve having a proximal portion, a distal portion and an intermediate portion between the distal and proximal portions. The sleeve includes an inner member applying a radial force on the sleeve for securement within the esophagus, and a skirt connected to the sleeve to block acid backup from the stomach while not inhibiting passage of food into the stomach.

In some embodiments, the inner member is formed in a spiral shape and in some embodiments can be in the form of a spiral wire. The spiral configuration can have a double helix configuration. In other embodiments the inner member can include a mesh or stent.

In some embodiments, the sleeve has a retrieval structure at a proximal portion for retrieval of the sleeve.

The device in some embodiments can include a plurality of tines extending externally of the sleeve to grasp a wall of the esophagus.

The skirt can be positioned entirely internally of the sleeve. The skirt can also extend distally beyond a distal end of the sleeve. In some embodiments, the skirt includes a plurality of overlapping flaps. The flaps in some embodiments are only positioned along an edge to reduce the internal diameter of the sleeve in a collapsed position.

In accordance with another aspect, the present invention provides a method for treating acid reflux comprising: providing a sleeve having an inner member applying a radial force on the sleeve and a plurality of flaps;
inserting the sleeve into the esophagus; and
leaving the sleeve in the esophagus so that food can pass through the flaps into the stomach while acid is blocked from passing from the stomach.

In some embodiments, the method includes the step of removing the sleeve after a period of time. The sleeve can have a plurality of tines which engage the wall of the esophagus to retain the sleeve in the esophagus. In some embodiments, the sleeve can include an outer covering material. In some embodiments, the sleeve can include a helical coil.

The sleeve in some embodiments can be inserted transorally; in other embodiments the sleeve can be inserted surgically through jejunal access.

The method can further comprise the steps of collapsing the sleeve to a reduced diameter in a delivery device and exposing the sleeve from the delivery device.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION OF PREFERRED EMBODIMENTS

Figure 1:
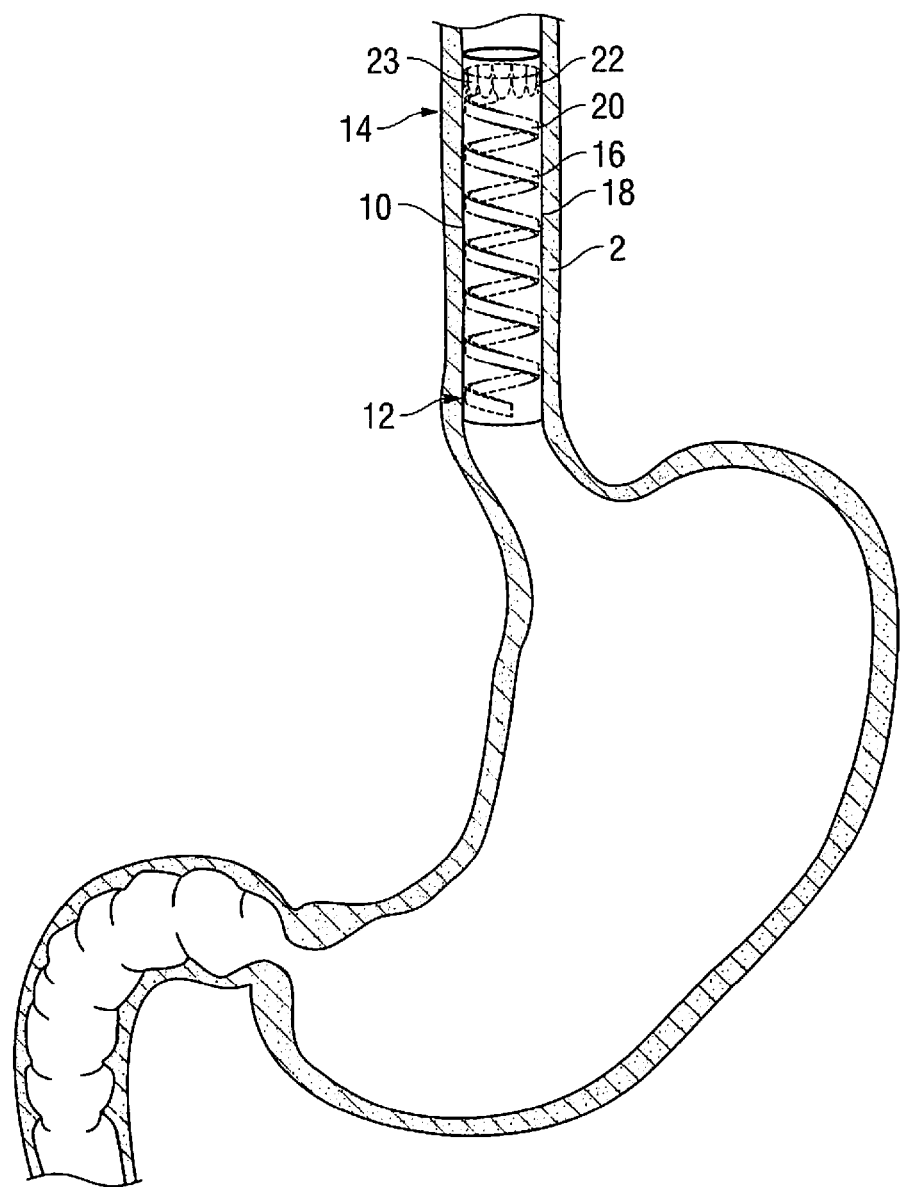
FIG. 1 is a side perspective view of a first embodiment of the esophageal sleeve of the present invention shown positioned in the esophagus.

Referring now to the drawings wherein like reference numerals identify similar structural features of the device disclosed herein, there is illustrated in FIG. 1 a device in the form of an esophageal sleeve in accordance with one embodiment of the subject invention and designated generally by reference numeral 10. As shown, the sleeve 10 is positioned in the esophagus 2 of a patient. The esophageal sleeve 10 is positioned and configured to limit acid reflux, while not inhibiting swallowing and passage of food into the stomach.

The sleeve 10 is composed of an inner member or body 16 forming a supporting structure and an outer covering member 18. For ease of understanding, a portion of the covering member is not shown in FIGS. 1-5B so the inner member can be shown. In the embodiment of FIG. 1, the inner member 16 is formed into a spiral shape, and can be formed from a wire. It has a first proximal portion 14 and a second distal portion 12. The sleeve 10 can be formed of a metal or plastic material. The spirals (coils) 20 of the inner member 10, as do the spirals of the other sleeves disclosed herein, exert a radial force on the outer covering member and esophageal wall to retain the sleeve 10 in place. A skirt 22 at the proximal portion 14 of the device 10 has a series of flaps 23 which move between an open position to enable swallowing and a closed position to block acid reflux, i.e., block backing up of contents of the stomach. Although the skirt 22 is shown at the proximal portion it could be located in other regions, e.g., the intermediate or distal portion of the device 10. Skirts of the other embodiments disclosed herein can also be located in proximal, intermediate or distal regions of the device.

The sleeve 10 can be removable to advantageously provide a temporary device. Consequently, the sleeve 10, or any of the other sleeves disclosed herein, can be placed in the body for a limited amount of time if desired. If complications arise, the sleeve 10 can easily be removed. The sleeve is preferably advantageously inserted transorally thereby providing a minimally invasive insertion method for acid reflux treatment.

Figure 2A:
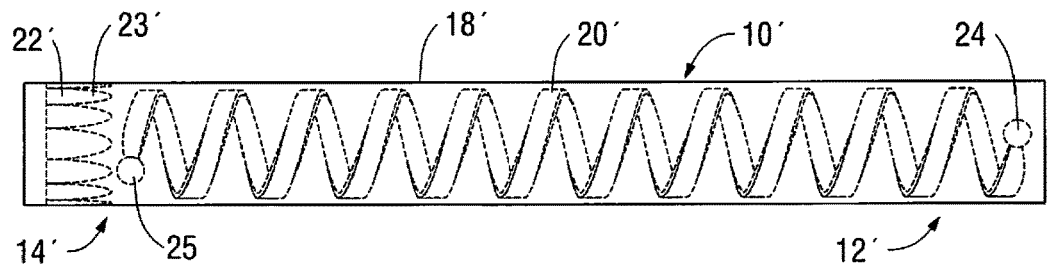
FIG. 2A is a side view of an alternate embodiment of the sleeve of the present invention.

The sleeve in some embodiments can have a retrieval structure, such as retrieval structure 25 at proximal portion 14' and/or retrieval structure 24 at distal portion 12' of sleeve 10' of FIG. 2A. In this embodiment of FIG. 2A, the retrieval structures 24, 25 are in the form of a ball at the ends of coil 20' which can be grasped by a retrieval tool. In this way, the sleeve 10' can be easily removed from the esophagus, thereby advantageously providing a temporary device for treating acid reflux. In all other respects, sleeve 10' is identical to sleeve 10 and includes covering member 18' and skirt 22' with flaps 23'. Note components corresponding to FIG. 1 are labeled with "prime" designations.

Figure 2B:
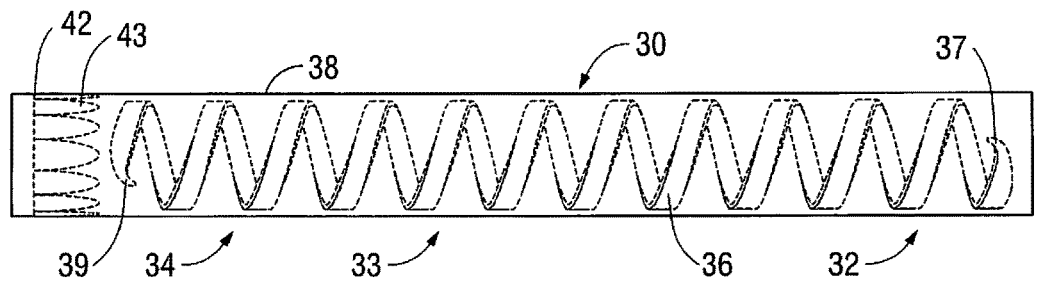
FIG. 2B is a side view of another alternate embodiment of the sleeve of the present invention.

In the alternate embodiment of FIG. 2B, the retrieval structure is in the form of a hook rather than a ball tip. More specifically, sleeve 30 has a proximal portion 34, a distal portion 32 and an intermediate portion 33. A retrieval structure in the form of a hook 37 is provided at the distal portion 32 of coil 36 and/or a hook 39 is provided at the proximal portion 34 of coil 36 for grasping by a retrieval tool for removal of the sleeve 30. Note the hook, ball or other retrieval structures disclosed herein to facilitate removal of the sleeve can be utilized with any of the sleeves disclosed herein. In all other respects, sleeve 30 is identical to sleeve 10 and has a skirt 42 with flaps 43 (similar to skirt 22) and a coil 36 within covering material 38.

It should be appreciated that although each of the sleeves disclosed herein are shown with a uniform configuration, it is also contemplated that the pitch and/or width of the coiled sections can vary in the sleeve.

Figure 5A:
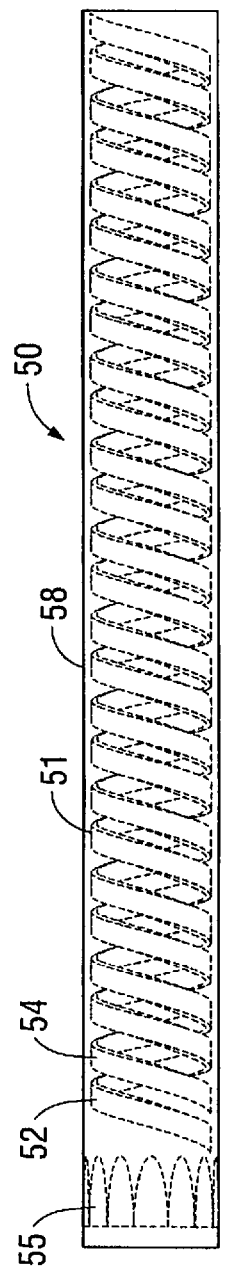
FIG. 5A is a side view of another alternate embodiment of the sleeve of the present invention.
Figure 5B:
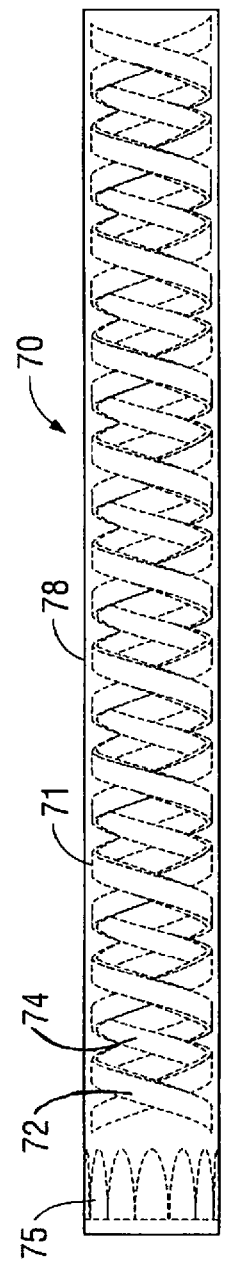
FIG. 5B is a side view of another alternate embodiment of the sleeve of the present invention.

In the alternate embodiment of FIG. 5A, sleeve 50 has an inner member 51 in the form of a double spiral 52 and 54, each wound in the same direction. Sleeve 50 is otherwise identical to sleeve 10 and includes a covering material 58 and a skirt 55 which functions for example like skirt 22. In the alternate embodiment of FIG. 5B, inner member 71 has a double helix structure with helix 72 and 74 of sleeve 70 wound in opposite directions forming sleeve 70. Sleeve 70 is otherwise identical to sleeve 10 and includes a covering material 78 and a skirt 75 which can be identical to skirt 22. As in other embodiments of the coils disclosed herein, the coils exert a radial force on the covering material and esophageal wall to retain the sleeve.

Figure 3:
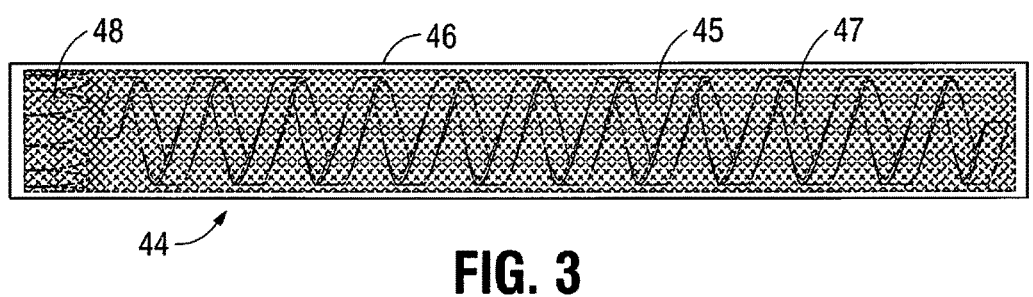
FIG. 3 is a side view of another alternate embodiment of the sleeve of the present invention.

In the embodiment of FIG. 3, an internal mesh 45 is provided inside the covering material 46 of the sleeve 44. The mesh 45 can be used in conjunction with coil 47 or instead of coil 47, with the mesh providing a radial force against the covering material and esophageal wall to retain it in the esophagus. That is, the mesh itself can provide sufficient radial force to retain the sleeve in the esophagus or a coil, such as any of the coils disclosed herein, can be embedded in the mesh to enhance and/or provide a radial retention force for sleeve 44. A skirt 48 as in the embodiments disclosed herein, e.g., identical to skirt 22, is contained within covering material 46.

Figure 4:
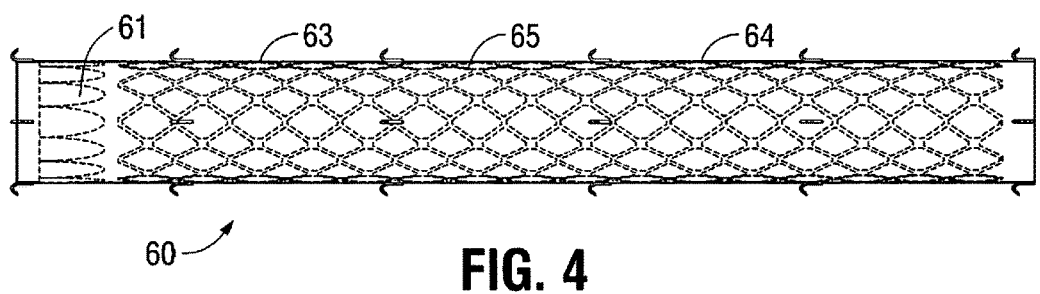
FIG. 4 is a side view of another alternate embodiment of the sleeve of the present invention.

In the embodiment of FIG. 4, instead of a coil, a stent-like body 65 is provided within covering material 63 of sleeve 60. The stent 65 has a plurality of struts forming closed cells and when positioned in its expanded position after delivery it exerts a radial force on the covering material 63 and esophageal wall. That is, the body 65 can be made of shape memory material and have a reduced diameter configuration for insertion and return to its larger diameter shape memorized position within the esophagus to exert a radial retention force. Skirt 61, as in the embodiments disclosed herein, e.g., identical to skirt 22, is positioned within covering material 63.

Figure 6A:
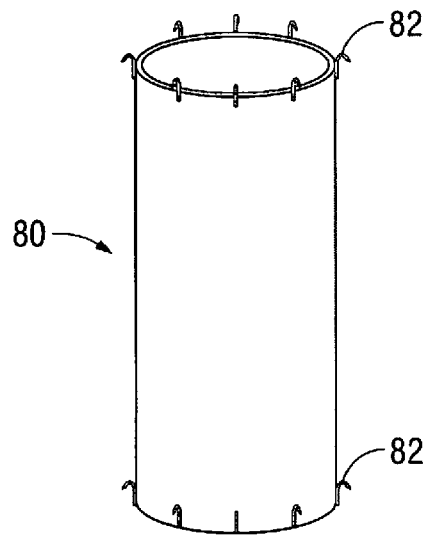
FIG. 6A is a side perspective view of another alternate embodiment of the sleeve of the present invention.
Figure 6B:
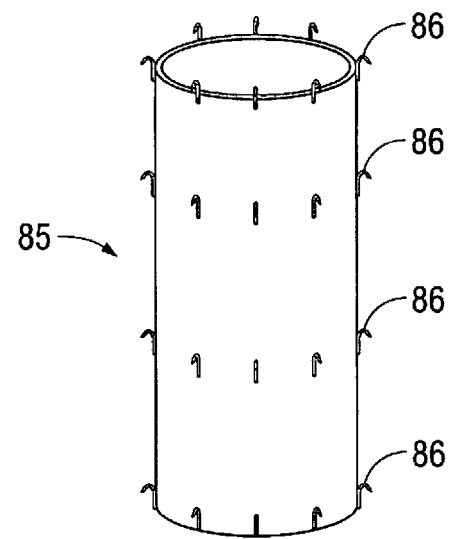
FIG. 6B is a side perspective view of another alternate embodiment of the sleeve of the present invention.

The sleeves disclosed herein can include retaining structure to enhance retention of the sleeve in the esophagus. As noted above, the coil (or mesh or stent) provides a radial force against the esophageal wall to retain the sleeve in the esophagus. However, if desired, further retention can be achieved thought a series of tines or hooks. In the embodiment of FIG. 6A, the tines 82 extending from sleeve 80 are formed at the distal end and proximal end. In the embodiment of FIG. 6B, additional tines are provided so the tines 86 of sleeve 85 are in the proximal, intermediate and distal regions of the sleeve 85. Sleeves 80 and 85 can contain the inner member, skirt and covering material of any of the embodiments disclosed herein. Stated another away, the tines of FIG. 6A or 6B, or other tine arrangements, can be utilized with any of the sleeve embodiments disclosed herein. FIG. 4 shows an example of tines 64 used with the embodiment of an internal stent-like body.

Figure 7:
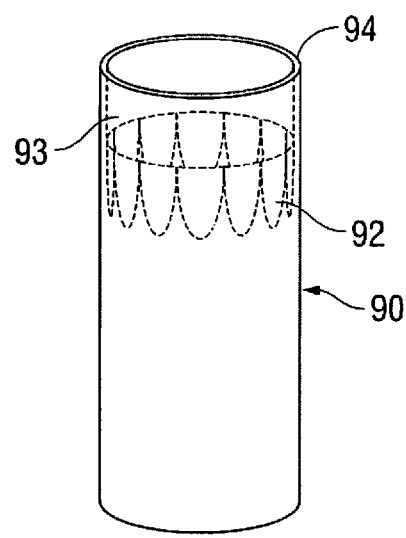
FIG. 7 is a side perspective view of another alternate embodiment of the sleeve of the present invention.
Figure 11:
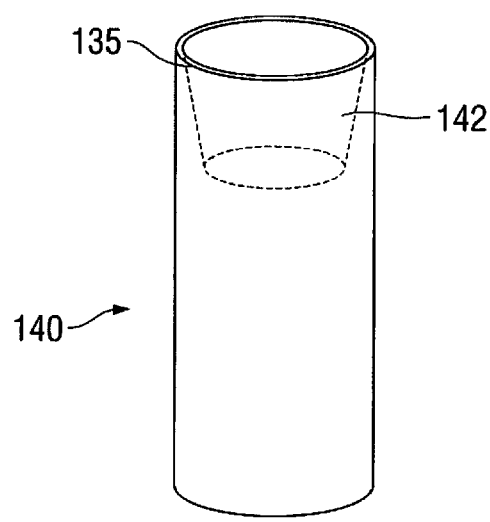
FIG. 11 is a side perspective view of another alternate embodiment of the sleeve of the present invention.
Figure 12:
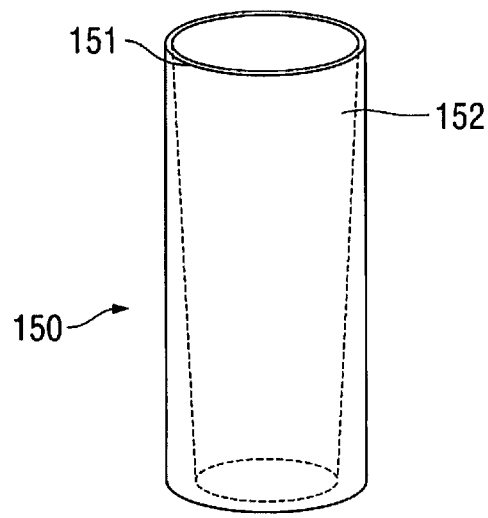
FIG. 12 is a side perspective view of another alternate embodiment of the sleeve of the present invention.
Figure 13:
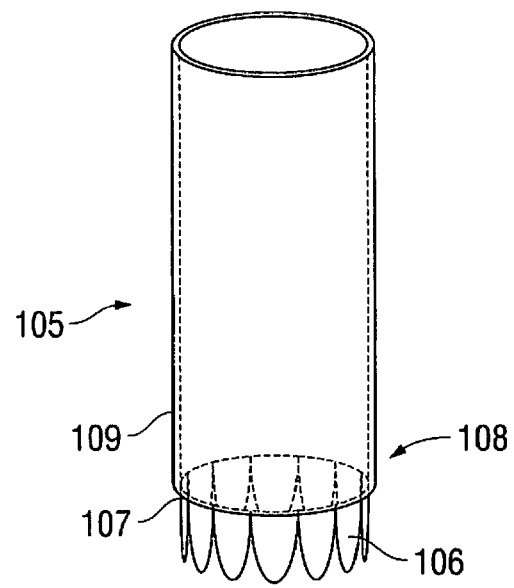
FIG. 13 is a side perspective view of another alternate embodiment of the sleeve of the present invention.
Figure 14:
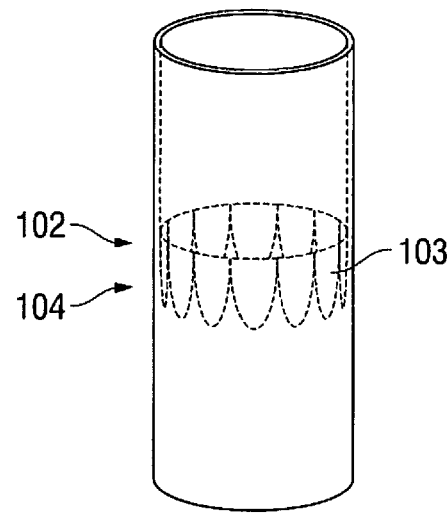
FIG. 14 is a side perspective view of another alternate embodiment of the sleeve of the present invention.

Alternative skirt configurations and alternative skirt locations are illustrated in FIGS. 7-15. In the embodiment of FIG. 7, skirt 92 of sleeve 90 is spaced distally from the proximal edge 94 of covering material 93, In FIG. 14, skirt 103 is positioned in an intermediate region 104 of sleeve 102. In FIG. 13, skirt 106 is spaced at a distal region 108 of sleeve 105, and extends distally beyond the distal edge 107 of covering material 109. By having the flaps extend outside the sleeve it reduces the collapsed outside diameter of the sleeve. Note these various skirt locations can be utilized with any of the sleeves disclosed herein and the skirts have flaps to function to enable swallowing and close to block back flow of stomach contents and acid.

Figure 8:
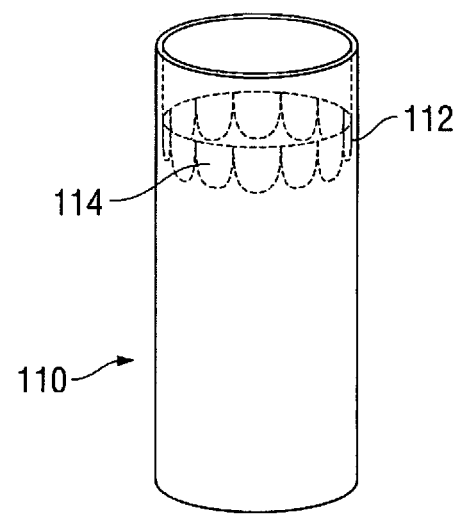
FIG. 8 is a side perspective view of another alternate embodiment of the sleeve of the present invention.
Figures 9, 10:
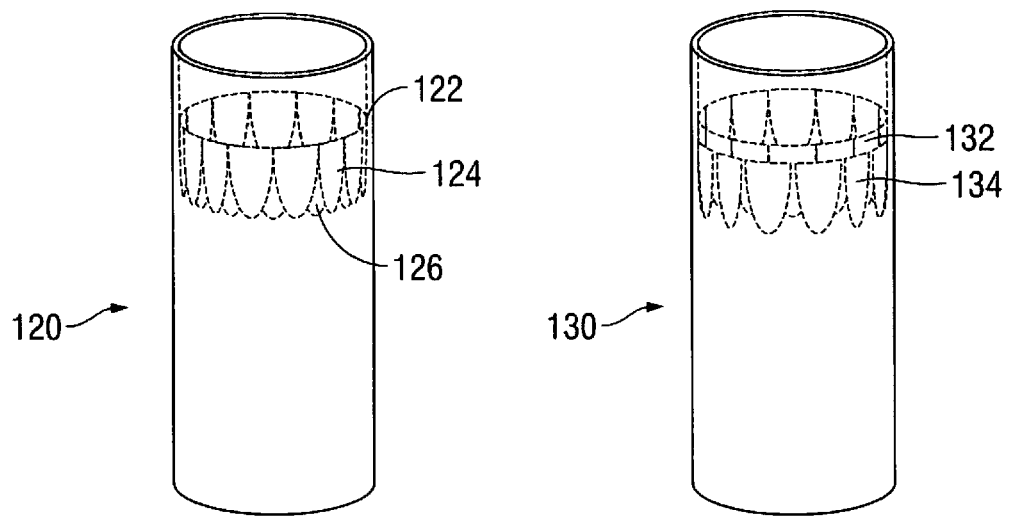
FIG. 9 is a side perspective view of another alternate embodiment of the sleeve of the present invention.
FIG. 10 is a side perspective view of another alternate embodiment of the sleeve of the present invention.

In addition to various locations, different skirt structures can be utilized. In the embodiment of FIG. 8, skirt 112 of sleeve 110 has shorter flaps 114. In the embodiment of FIG. 9, skirt 122 of sleeve 120 has a double layer of flaps with a series of flaps 124 forming the outer layer and a series of flaps 126 forming an inner layer. Flaps 134 of skirt 132 of sleeve 130 of FIG. 10 are arranged in a "roof shingle" type configuration. These various skirt structures open to enable swallowing and close to block backup, and can be used with any of the sleeves disclosed herein.

Figure 15:
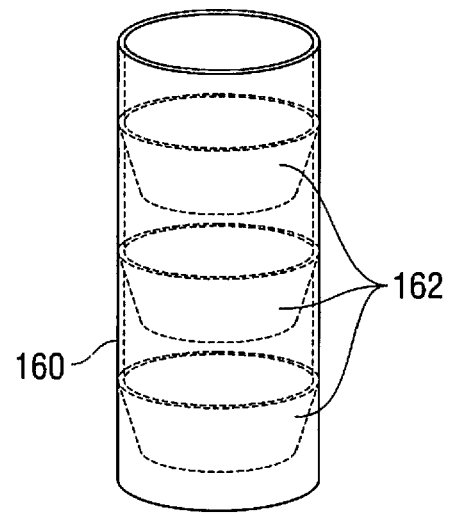
FIG. 15 is a side perspective view of another alternate embodiment of the sleeve of the present invention.

In the foregoing embodiments, the blocking member is in the form of a skirt having a series of flaps movable between open and closed configurations. When closed, the flap tips can be contiguous or alternatively can overlap. Additionally, multiple layers of flaps can be utilized. As an alternative to the flaps, the blocking member can be in the form of a solid skirt which is foldable or collapsible to a closed configuration. Such solid skirts are shown for example in the embodiments of FIGS. 11, 12, and 15. Note the internal retention structure has been removed from FIGS. 7-15 for clarity, it being understood the coils, braids or stent-like body, or other internal structure, can be used with the sleeves of FIGS. 7-15 to provide a radial retention force. In the embodiment of FIG. 11, the skirt 142 of sleeve 140 is conical in shape, with the base 135 in the more proximal position. In the embodiment of FIG. 12, the skirt 152 extends a substantial length of the sleeve 150 with the base 151 in the more proximal position. In FIG. 15, a series of conical shaped skirts 162 are positioned along the length of sleeve 160, axially spaced from one another. These solid skirts are shown, as are the skirts with flaps, in the open configuration. These solid skirts can be used with any of the sleeves disclosed herein.

As noted above, in the various embodiments disclosed herein using a spiral support within the covering material, the width of the spirals and/or pitch can be varied from that shown or varied along its length so the spirals are not uniform.

The sleeves described herein can be formed of a metallic or non-metallic, e.g., plastic, material. Additionally, the sleeves disclosed herein can be provided with the hook, ball tip or other retrieval structure to facilitate removal. Moreover, the sleeves can have areas of different cross sectional dimension.

Preferably, the sleeve has a cross-sectional dimension (or diameter) in its normal state that is slightly greater than the internal diameter of the esophagus. For delivery, the sleeve is placed within a delivery device and compressed to a smaller cross-sectional dimension providing a reduced profile for delivery (insertion). The delivery device is advanced into the esophagus. The delivery device (and sleeve) can be advanced transorally in some embodiments. The sleeve is exposed from the delivery device and then expands to its normal cross-sectional dimension. Being slightly greater than the internal diameter of the esophageal wall, in its normal position it provides a sufficient radial force against the esophageal wall to thereby be retained within the esophagus.

The covering material is attached to the coil (spiral section) or other internal structure in a variety of known methods. This internal structure forms the support section (internal support) for the covering material.

As noted above, the spiral section provides a support for the covering section. In alternate embodiments, a stent can be positioned within the covering material. In other alternate embodiments, a mesh material can provide an internal supporting structure for the covering section.

In use, the sleeve delivery device is preferably inserted transorally and advanced into the esophagus. The sleeve is withdrawn (retracted in a proximal direction) to expose the sleeve (or the sleeve is moved distally out of the delivery device or both the sleeve is moved distally and the delivery device retracted) for placement of the sleeve in the esophagus. In some embodiments, the delivery device can include an endoscope to provide visualization during advancement and placement of the sleeve.

The foregoing sleeves can alternatively be inserted via a jejunal access or through open surgery.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A device for treating acid reflux comprising a sleeve configured and dimensioned for insertion into an esophagus of a patient, the sleeve having a proximal portion, a distal portion and an intermediate portion between the distal and proximal portions, the sleeve including an inner member extending from a proximal region of the sleeve to a distal region of the sleeve, the inner member applying a radial force on the sleeve along a length thereof for securement within the esophagus, and a skirt connected to the sleeve to block acid backup from a stomach while not inhibiting passage of food into the stomach, the skirt positioned within the sleeve and axially spaced from the inner member, the skirt movable between an open position and a closed blocking position within the sleeve, wherein the skirt includes a plurality of flaps extending toward the inner member when food passes through the skirt toward the stomach.

2. The device of claim 1, wherein the inner member is formed in a spiral shape.

3. The device of claim 1, wherein the sleeve has a retrieval structure at the proximal portion for retrieval of the sleeve.

4. The device of claim 3, wherein the retrieval structure includes a hook or ball tip.

5. The device of claim 1, wherein the inner member comprises a helical coil in the form of a wire.

6. The device of claim 1, wherein the inner member includes a spiral configuration having a double helix configuration.

7. The device of claim 1, further comprising a plurality of tines extending externally of the sleeve to grasp a wall of the esophagus.

8. The device of claim 1, wherein the skirt is positioned proximal of the inner member.

9. The device of claim 8, wherein the sleeve has a proximal edge and the skirt is positioned distal of the proximal edge.

10. The device of claim 1, wherein the plurality of flaps overlap.

11. The device of claim 1, wherein the inner member comprises a mesh.

12. The device of claim 1, wherein the inner member comprises a stent-like body.

13. The device of claim 1, further comprising a second skirt within the inner member axially spaced from the skirt.

* * * * *